US00PP26369P3

(12) United States Plant Patent
Moore

(10) Patent No.: US PP26,369 P3
(45) Date of Patent: Feb. 2, 2016

(54) RED RASPBERRY PLANT NAMED 'CASCADE HARVEST'

(50) Latin Name: ***Rubus idaeus* L.**
Varietal Denomination: Cascade Harvest

(71) Applicant: Washington State University, Pullman, WA (US)

(72) Inventor: Patrick Peder Moore, Puyallup, WA (US)

(73) Assignee: Washington State University, Pullman, WA (US)

( * ) Notice: Subject to any disclaimer, the term of this patent is extended or adjusted under 35 U.S.C. 154(b) by 104 days.

(21) Appl. No.: 13/999,114

(22) Filed: Jan. 13, 2014

(65) Prior Publication Data

US 2015/0201538 P1 Jul. 16, 2015

(51) Int. Cl.
*A01H 5/00* (2006.01)

(52) U.S. Cl.
USPC ..... Plt./204

(58) Field of Classification Search
USPC ..... Plt./203, 204
See application file for complete search history.

*Primary Examiner* — Susan McCormick Ewoldt
(74) *Attorney, Agent, or Firm* — Christensen O'Connor Johnson Kindness PLLC

(57) ABSTRACT

This invention relates to a new and distinct variety of red raspberry plant (*Rubus idaeus* L.) named 'Cascade Harvest' adapted to the raspberry production area of the Pacific Northwest. 'Cascade Harvest' is primarily characterized by suitability for machine harvestability, tolerance to root rot, resistance to raspberry bushy dwarf virus and large, conical fruit that is longer than it is broad.

5 Drawing Sheets

STATEMENT REGARDING FEDERALLY-SPONSORED RESEARCH

This invention was made with government support under Grant number 58-5358-9-440 awarded by the United States Department of Agriculture. The government has certain rights in the invention.

Latin name: Botanical/commercial classification: *Rubus idaeus* L.

Varietal denomination: The varietal denomination of the claimed raspberry variety is 'Cascade Harvest'.

FIELD OF THE INVENTION

This invention concerns a new and distinct cultivar of red raspberry plant having a varietal denomination of 'Cascade Harvest' with a botanical name of *Rubus idaeus* L.

BACKGROUND OF THE INVENTION

Raspberries are an economically important crop in the United States. Accordingly, there exists a need to develop new raspberry varieties with improved characteristics, such as disease resistance.

SUMMARY OF THE INVENTION

The present invention relates to a new and distinct floricane bearing (summer fruiting on second year canes) red raspberry variety designated as 'Cascade Harvest'. The variety is botanically known as *Rubus idaeus* L. The new and distinct variety of red raspberry originated from a hand-pollinated cross of the patented variety 'Cascade Dawn' (U.S. Plant Pat. No. 17,985) (used as the female parent) and Washington State University selection 'WSU 1145' (unpatented) (used as the male parent), which cross was made in Year 1 at the Washington State University Puyallup Research and Extension Center. Seeds were germinated in the winter of Year 1-Year 2 and the resulting seedlings planted in Year 2. 'WSU 1507', which is presently designated as 'Cascade Harvest', was selected in Year 4 and asexually propagated in tissue culture using meristem cultures from axillary buds of primocanes. This selection was planted in non-replicated plots with cooperating growers in Year 5, Year 6, Year 8 and Year 13. The plantings were maintained by growers using typical commercial methods and fruit machine harvested. The plantings were subjectively evaluated weekly for adaptation to machine harvesting for two fruiting seasons. In all harvest seasons this selection machine harvested well and was productive with large fruit size. This selection was tested for tolerance to root rot and resistance to raspberry bushy dwarf virus. Plants and fruit of this new variety have remained true to type through successive generations of asexual propagation. 'WSU 1507' is being named and released as 'Cascade Harvest' and is the subject of this invention.

'Cascade Harvest' is adapted to raspberry production areas of the Pacific Northwest. There have been no observed winter damage in our tests, therefore winter hardiness is unknown.

The following traits have been repeatedly observed and are determined to be unique characteristics of 'Cascade Harvest,' which in combination distinguish this raspberry plant as a new and distinct variety:

1. Large fruit size
2. Conic fruit shape, with fruit longer than broad
3. Tolerance to root rot
4. Resistance to raspberry bushy dwarf virus
5. Suitability for machine harvesting 'Cascade Harvest' is distinguished from its parent, 'Cascade Dawn', by having smaller drupelets, lighter fruit color and suitability for machine harvesting.

'Cascade Harvest' is distinguished from its parent, 'WSU 1145', by having longer fruit, a greater fruit length to width ratio, superior fruit flavor and resistance to raspberry bushy dwarf virus.

'Cascade Harvest' is distinguished from the most commonly grown red raspberry in the Pacific Northwest, 'Meeker' (unpatented), by having more drupelets per fruit, smaller drupelets and smaller seed weights, earlier bud break, tolerance to root rot and resistance to raspberry bushy dwarf virus.

'Cascade Harvest' is distinguished from 'Willamette' (unpatented) by its larger, lighter colored fruit, greater fruit length to width ratio, later harvest season, greater yield, and tolerance to root rot.

BRIEF DESCRIPTION OF THE DRAWINGS

The accompanying figures illustrate typical characteristics of the new variety 'Cascade Harvest' and are true to color as it is reasonably possible with color reproductions of this type. Color in the photographs may differ slightly from the color value cited in the detailed botanical description, which accurately describes the color of 'Cascade Harvest'. When objects could be accurately measured with an 8 mm diameter measuring opening (leaves, fruit and some canes), color was measured with a Minolta CR-400 Colorimeter, which measures color in L*, a*, b* color coordinates. Calibration was performed using a standard white plate supplied by the manufacturer. These L*, a*, b* coordinates were converted and are presented in Munsell color notation. For all other color measurements, color was compared with Royal Horticultural Society Colour Chart color plates and presented using Royal Horticultural Society Colour Chart designations.

DETAILED BOTANICAL DESCRIPTION

Figure 1:
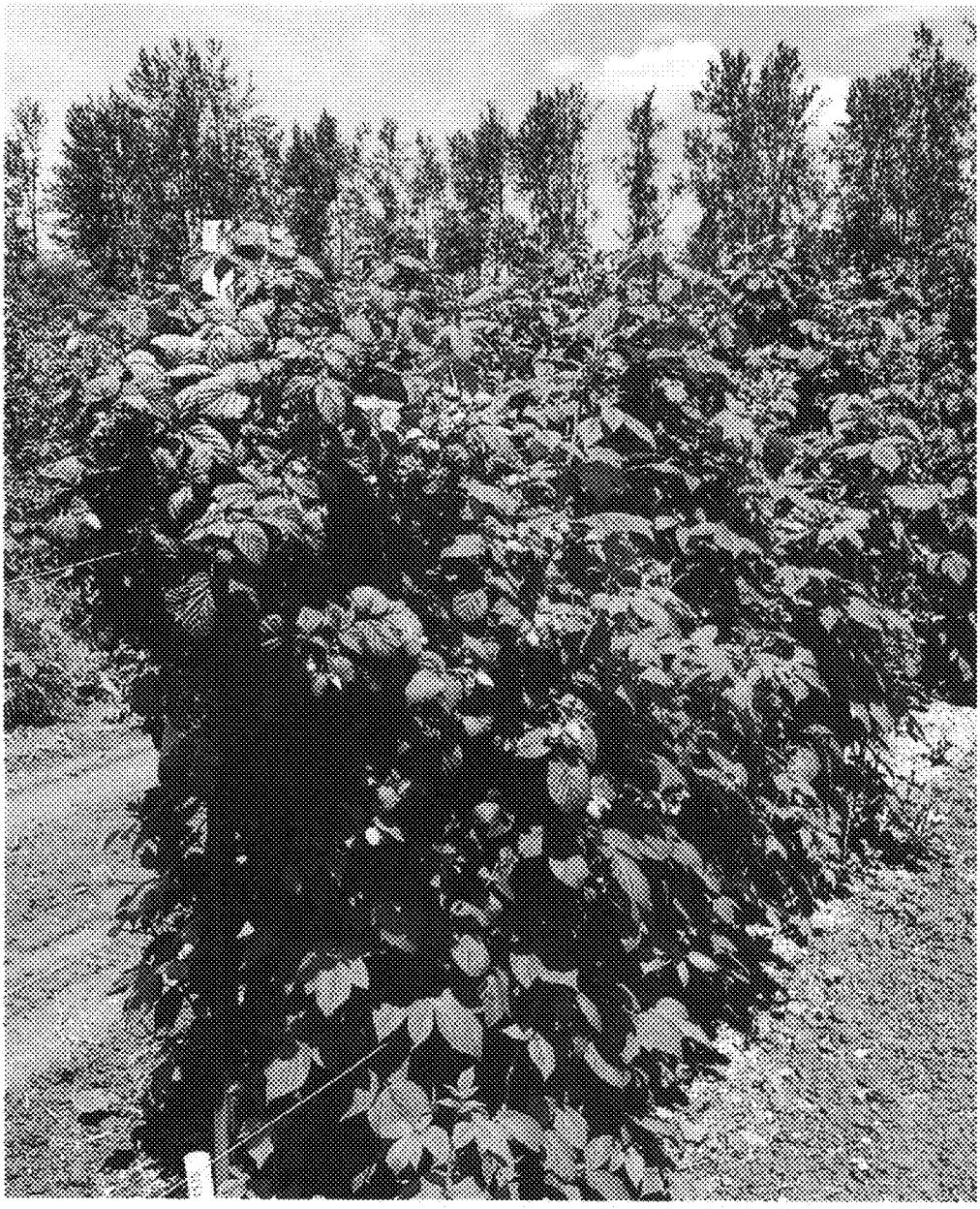
FIG. 1 illustrates the plant of 'Cascade Harvest', showing the growth habit of the plant and display of the fruit on 27 June, Year 15.
Figure 2:
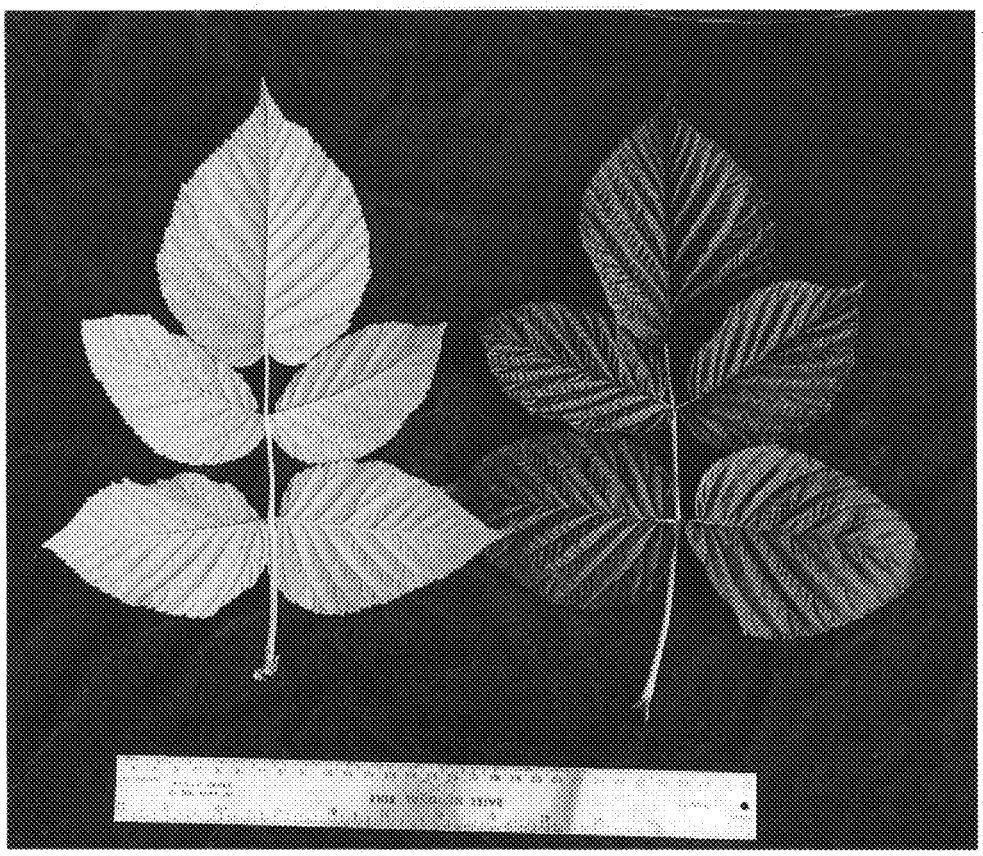
FIG. 2 illustrates the primocane leaves of 'Cascade Harvest' on 21 July, Year 13. The upper, adaxial and lower, abaxial surfaces are shown on the right and left sides of the figure, respectively.
Figure 3:
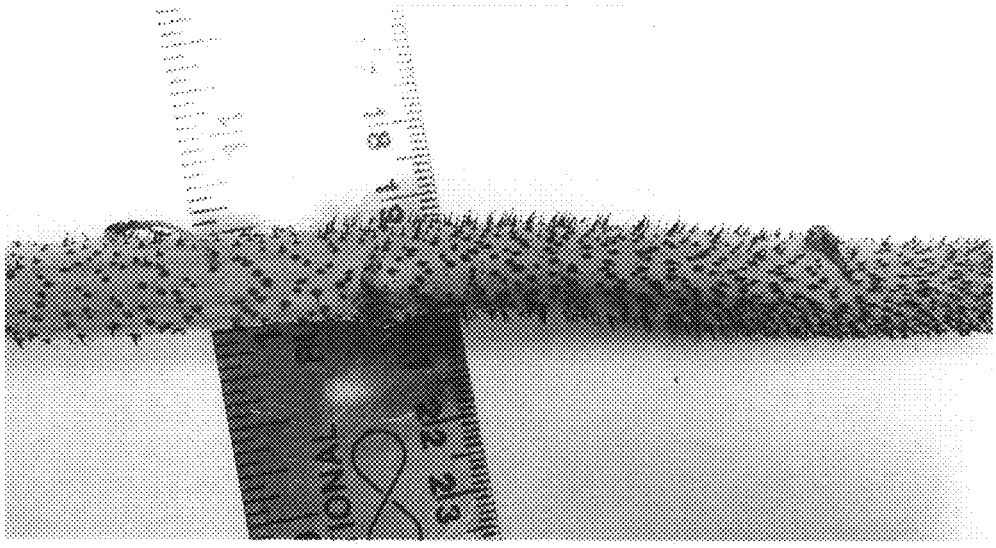
FIG. 3 illustrates the basal portion of a young primocane of 'Cascade Harvest' on 31 July, Year 15, showing the frequency and shape of the spines and spine base.
Figure 4:
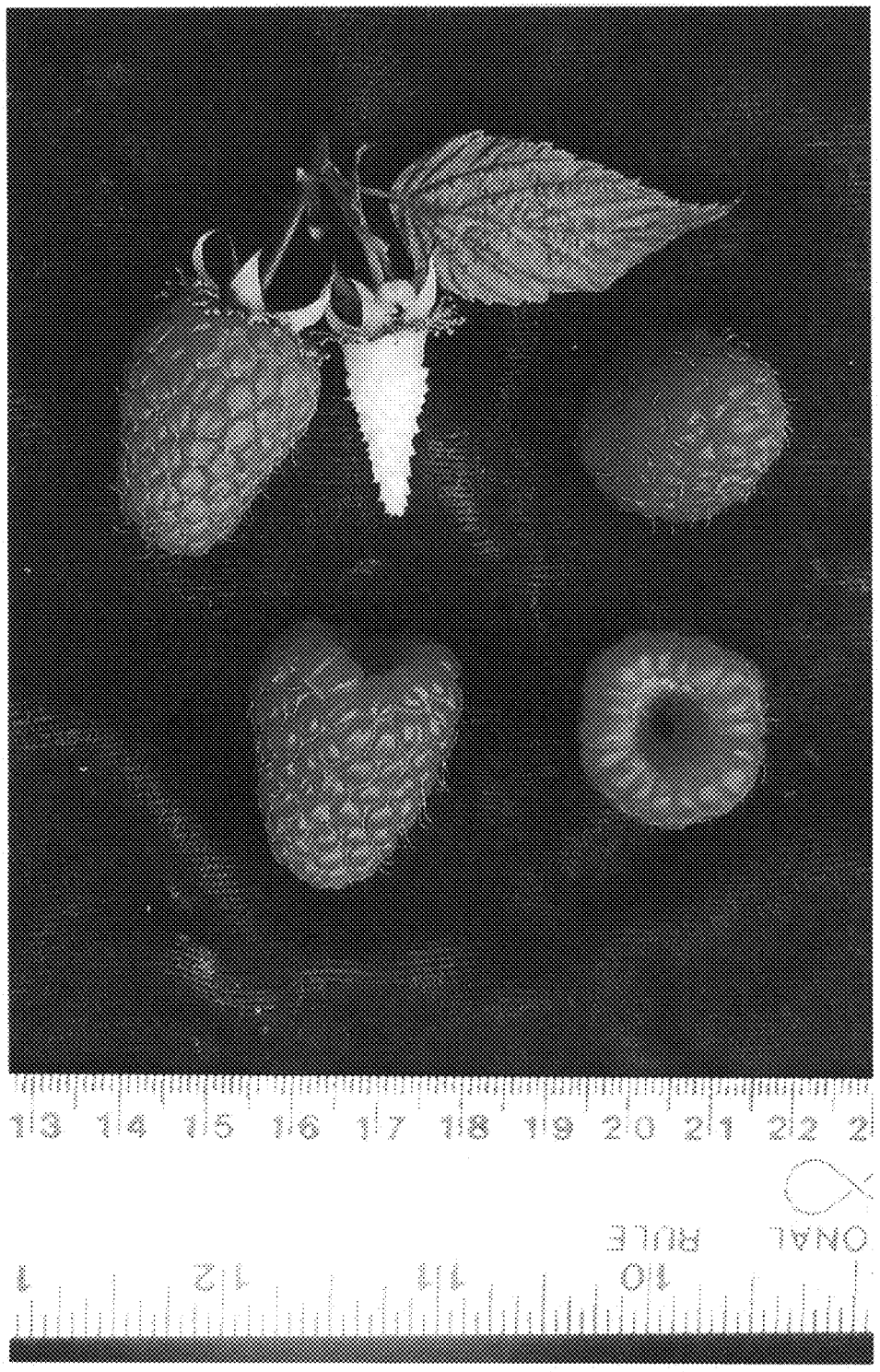
FIG. 4 illustrates the fruit and receptacle of 'Cascade Harvest' on 9 July, Year 15.
Figure 5:
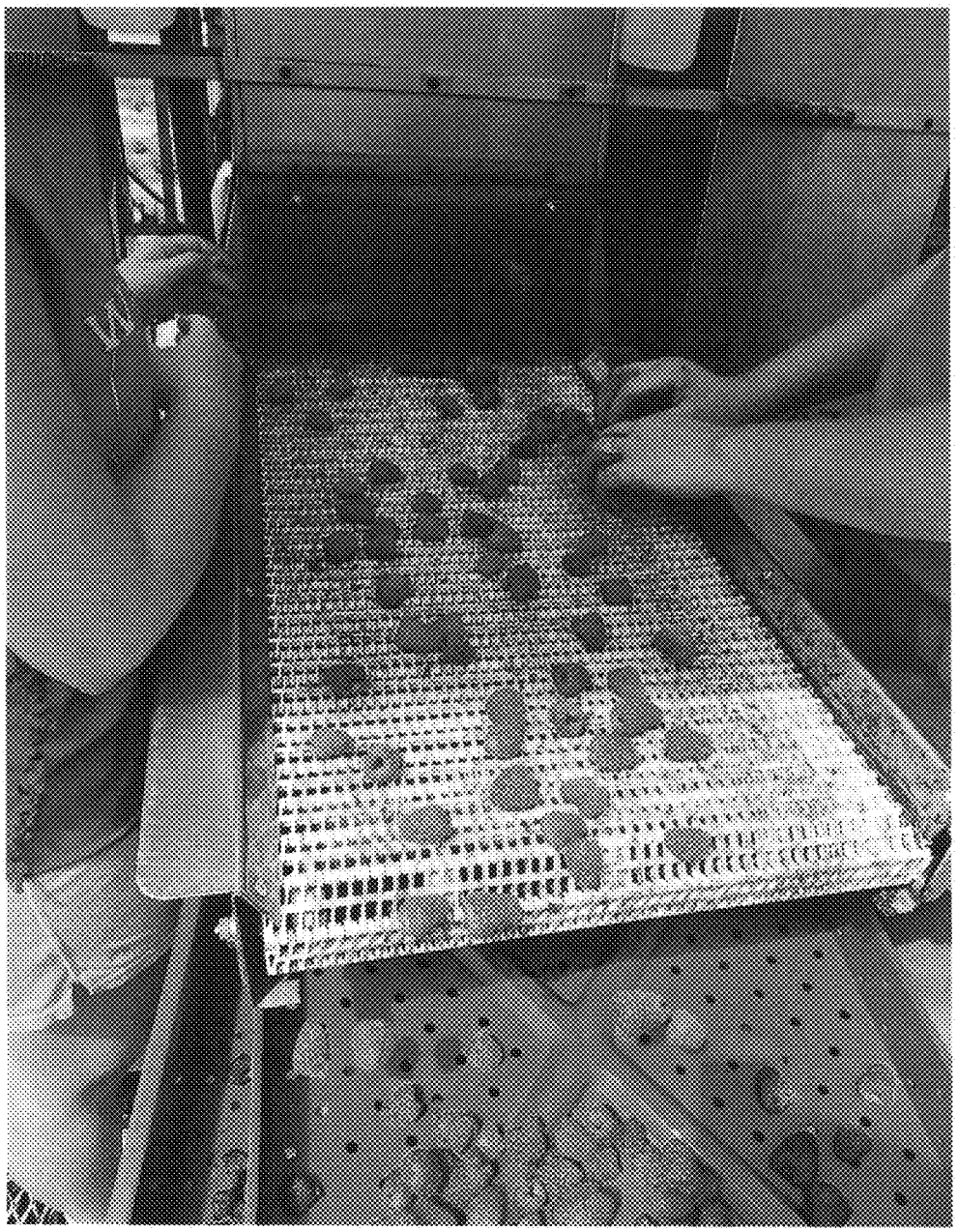
FIG. 5 illustrates the machine harvested fruit of 'Cascade Harvest' on 1 July, Year 16.

'Cascade Harvest' has not been observed under all possible environmental conditions and as such the characteristics may vary in detail depending on weather conditions, day length, soil type and location. The description is based on observations taken during Year 15 (except as noted) in Puyallup, Wash.

A comparison of fruit of 'Cascade Harvest' with its parents is given in Table 1. Fruit of 'Cascade Harvest' were longer in length and had a greater length to width ratio than 'WSU 1145' and the drupelets of 'Cascade Harvest' were smaller than 'Cascade Dawn'.

TABLE 1

Fruit morphological measurements for raspberry fruit harvested in Year 15 at Puyallup, WA, comparing 'Cascade Harvest' with its parents[z].

| | 'Cascade Harvest' | 'WSU 1145' | 'Cascade Dawn' |
|---|---|---|---|
| Fruit | | | |
| Weight (g) | 5.1 ab[y] | 4.5 b | 6.0 a |
| Length (mm) | 26.6 a | 20.8 b | 27.5 a |
| Width (mm) | 20.5 a | 22.2 a | 22.2 a |
| Length/width | 1.30 a | 0.94 b | 1.24 a |
| Fruit opening | | | |
| Length (mm) | 22.2 a | 14.9 b | 21.7 a |
| Width (mm) | 8.8 a | 10.0 a | 9.7 a |
| Length/width | 2.52 a | 1.48 b | 2.27 a |
| Drupelet | | | |
| Length (mm) | 4.7 b | 5.5 a | 5.7 a |
| Width (mm) | 3.6 a | 4.0 a | 4.2 a |
| Color | | | |
| Munsell Color | 5.2R3.0/6.0 | 5.2R3.1/6.6 | 5.4R2.5/4.8 |

[z]Five fruit of each cultivar were measured.

[y]Means within a row followed by the same letter are not significantly different at $P < 0.05$, by Tukey's Studentized Range Test (HSD).

The field performance of 'Cascade Harvest' is compared to 'Meeker' and 'Willamette' in Table 2. 'Cascade Harvest' had greater cumulative yield than 'Meeker' and 'Willamette', but was not statistically significant. Fruit weight averaged over the season of 'Cascade Harvest' was greater than 'Meeker' and 'Willamette' but not statistically different from 'Willamette' in Year 15. The harvest season for 'Cascade Harvest' was later than 'Willamette' and slightly earlier than 'Meeker'.

TABLE 2

Year 14 and Year 15 harvest data from Year 12 planted raspberries, Puyallup, WA.

| | | | Cascade Harvest' | 'Meeker' | 'Willamette' |
|---|---|---|---|---|---|
| Yield (t/a) | Year 15 | | 8.0 a[y] | 8.9 a | 6.9 a |
| | Year 14 | | 5.2 a | 3.3 a | 4.0 a |
| | Total | | 13.1 a | 12.2 a | 10.8 a |
| Fruit weight (g) | Year 15 | | 3.7 a | 3.1 b | 3.5 ab |
| | Year 14 | | 3.8 a | 2.8 b | 2.9 b |
| Fruit rot (%) | Year 15 | | 3.8 a | 4.5 a | 4.9 a |
| | Year 14 | | 11.8 a | 7.0 a | 7.2 a |
| Fruit firmness (g) | Year 15 | | 70 b | 71 b | 83 a |
| | Year 14 | | 90 a | 65 a | 72 a |
| Dates for percentage cumulative yield | | | | | |
| | Year 15 | 5% | Jul. 2 a | Jul. 4 a | Jun. 25 b |
| | | 50% | Jul. 14 a | Jul. 16 a | Jul. 5 b |
| | | 95% | Jul. 28 a | Jul. 30 a | Jul. 20 b |
| | Year 14 | 5% | Jul. 6 ab | Jul. 8 a | Jul. 4 b |
| | | 50% | Jul. 18 a | Jul. 20 a | Jul. 15 a |
| | | 95% | Aug. 1 a | Aug. 2 a | Jul. 27 b |
| Length of harvest season (days) | Year 15 | | 26 a | 27 a | 25 a |
| | Year 14 | | 26 a | 25 a | 23 a |

[z]Means based on three replications of three plants.

[y]Means within a row followed by the same letter are not significantly different at $P < 0.05$, by Tukey's Studentized Range Test (HSD).

Table 3 provides information on the plant and fruit characteristics of the new variety 'Cascade Harvest'. The table compares 'Cascade Harvest' with 'Meeker', the most widely planted raspberry variety in Washington.

TABLE 3

Plant and fruit characteristics of 'Cascade Harvest' and 'Meeker'

| | 'Cascade Harvest' | 'Meeker' |
|---|---|---|
| General (31 Jul., Year 15) | | |
| Plant height (m) | 1.57 | 1.65 |
| Plant width (m) | 1.27 | 1.32 |
| Self-fruitfulness | self | self |
| Time of bud break | 7 Feb., Year 15 | 22 Feb., Year 15 |
| Time of primocane emergence | 5 Apr., Year 15 | 5 Apr., Year 15 |
| Primocanes | | |
| Dormant (20 Feb., Year 15) | | |
| Length (m) | 2.72 | 3.11 |
| Cane diameter at ground (mm) | 15.2 | 11.6 |
| Cane diameter at 1.5 m from ground (mm) | 10.7 | 9.0 |
| Number of nodes | 63 | 66 |
| Internode length at 1.5 m from ground (mm) | 44 | 41 |
| Cane color (Munsell) | 5.1YR 4.0/5.2 | 8.2YR 4.3/3.4 |
| Immature canes (31 Jul., Year 15) | | |
| Number of canes/hill | 17 | 22 |
| Length (m) | 1.73 | 2.27 |
| Cane diameter at ground (mm) | 12.9 | 11.9 |
| Cane diameter at 1.2 m from ground (mm) | 7.3 | 9.9 |
| Number of nodes | 37.3 | 46.7 |
| Internode length at 1.2 m from ground (mm) | 62 | 64 |
| Immature cane color (RHS) | | |
| Predominant Color | 145C Yellow Green | 145B Yellow Green |
| Secondary Color | 60C Red Purple | 60A Red Purple |
| Primocane fruiting | none | none |
| Pubescence on canes | absent | slight |
| Floricanes (31 Jul., Year 15) | | |
| Diameter at base (mm) | 14.7 | 13.5 |
| Diameter at 1.2 m from ground (mm) | 9.4 | 9.8 |
| Internode length at 1.2 m from ground (mm) | 44 | 61 |
| Spines (31 Jul., Year 15) | | |
| Density at base of young shoots | dense | dense |
| Density at 1.2 m from ground | few or none | few |
| Color (RHS) | 187A Greyed Purple | 59B Red Purple |
| Length of spine | 2.0 mm | not measured |
| Length of spine base | 2.1 mm | not measured |
| Width of spine base | 1.7 mm | not measured |
| Color of spine base (RHS) | 187A Greyed Purple | not measured |
| Leaves (1 Aug., Year 15) | | |
| Primocane leaves | | |
| Number of leaflets | 5 | 5 |
| Petiole length (mm) | 65 | 57 |
| Rachis length (mm) | 39 | 36 |
| Stipule length (mm) | 8.1 | 8.7 |
| Leaflet margins | doubly serrated | doubly serrated |
| Leaflet overlap | occasionally overlap | commonly overlap |
| Terminal leaflet | | |
| Length (mm) | 105 | 105 |
| Width (mm) | 69 | 70 |
| Length/width | 1.52 | 1.50 |
| Petiolule length (mm) | 21 | 12 |
| Leaflet tip | cuspidate | cuspidate |
| Leaflet base | rounded to cordate | cunate |
| Distal Lateral Leaflet | | |
| Length(mm) | 90 | 78 |
| Width (mm) | 46 | 37 |
| Length/width | 1.96 | 2.11 |

TABLE 3-continued

Plant and fruit characteristics of 'Cascade Harvest' and 'Meeker'

| | 'Cascade Harvest' | 'Meeker' |
|---|---|---|
| Petiolule length (mm) | 0 | 0 |
| Leaflet tip | cuspidate | cuspidate |
| Leaflet base | obtuse to oblique | oblique |
| Basal Lateral Leaflet | | |
| Length (mm) | 100 | 94 |
| Width (mm) | 60 | 54 |
| Length/width | 1.67 | 1.74 |
| Petiolule length (mm) | 3.3 | 2.8 |
| Leaflet tip | cuspidate | cuspidate |
| Leaflet base | obtuse to oblique | obtuse to oblique |
| Color (Munsell) | | |
| Upper surface | 5.9GY 3.1/3.5 | 6.2GY 3.4/4.0 |
| Lower surface | 5.1GY 5.1/2.0 | 5.4GY 5.7/1.6 |
| Floricane leaves | | |
| Number of leaflets | 3 | 3 |
| Petiole length (mm) | 43 | 44 |
| Leaflet margins | doubly serrated | doubly serrated |
| Terminal leaflet | | |
| Length (mm) | 87 | 95 |
| Width (mm) | 68 | 49 |
| Length/width | 1.28 | 1.94 |
| Basal lateral leaflet | | |
| Length (mm) | 77 | 80 |
| Width (mm) | 48 | 43 |
| Length/width | 1.60 | 1.86 |
| Color (Munsell) | | |
| Upper surface of leaflet | 5.7GY 3.4/4.1 | 6.1GY 3.4/3.7 |
| Lower surface of leaflet | 4.7GY 5.5/1.9 | 5.3GY 5.2/2.2 |
| Flower and fruiting lateral (3 Jul., Year 15) | | |
| Number of petals | 5 | 5 |
| Number of sepals | 5 | 5 |
| Petal color | white 155D | white 155D |
| Number of anthers | 87 | 76 |
| Flower diameter petal-petal (mm) | 10.3 | 9.3 |
| Flower diameter sepal-sepal (mm) | 20.7 | 20.0 |
| Flower fragrance | none noted | none noted |
| Pedicel length (mm) | 18.0 | 18.0 |
| Lateral length (cm) | 69 | 64 |
| Number of nodes/lateral | 16.7 | 17.0 |
| Number of fruiting nodes/lateral | 9.0 | 11.3 |
| Number of fruit/lateral | 24.0 | 33.0 |
| Number of fruit/fruiting node | 2.7 | 2.9 |
| Fruit measurements (July, Year 16) | | |
| Fruit weight (g) | 3.61 | 3.65 |
| Drupelet number | 122 | 91 |
| Drupelet weight (mg) | 30 | 40 |
| Individual seed weight (mg) | 1.37 | 1.76 |

Machine harvested fruit was collected on five dates during the Year 8 harvest season from a test planting established in Year 6 at Burlington, Wash. (Table 4). 'Cascade Harvest' had slightly less total anthocyanins than 'Meeker' and was similar to 'Meeker' for soluble solids, pH and titratable acidity. 'Cascade Harvest' had less anthocyanins and less titratable acidity than 'Willamette'.

TABLE 4

Anthocyanin content, soluble solids, pH and titratable acidity of raspberry fruit machine harvested in Year 8 at Burlington, WA[z]

| Cultivar | 'Cascade Harvest' | 'Meeker' | 'Willamette' |
|---|---|---|---|
| Anthocyanin content (mg/g fruit)[y] | 52.8 c[w] | 60.8 b | 91.6 a |
| Soluble solids (%) | 8.1 ab | 9.3 a | 7.3 b |
| pH | 3.27 ab | 3.35 a | 3.08 b |
| Titratable acidity[x] | 0.93 b | 0.99 b | 1.33 a |

[z]Fruit samples of approximately 300 g collected on each harvest date.

Raspberry plots were machine harvested on 20 and 28 Jun. and 6, 11 and 18 Jul., Year 8.

[y]Total anthocyanins determined spectrophotometrically from acidified ethanol extracts and expressed as cyanidin 3-galactoside.

[x]Acidity expressed as % citric acid.

[w]Means within a row followed by the same letter are not significantly different at $P < 0.05$, by Tukey's Studentized Range Test (HSD).

'Cascade Harvest' was planted in non-replicated plots with cooperating growers in Year 5, Year 6, Year 8 and Year 13. The plantings were maintained by growers using typical commercial methods and the fruit machine harvested. The plantings were subjectively evaluated for adaptation to machine harvesting weekly during the harvest season for two fruiting seasons. In all harvest seasons 'Cascade Harvest' machine harvested well and was productive with large fruit size. Based on these evaluations, fruit of 'Cascade Harvest' is suitable for machine harvesting.

'Cascade Harvest' was evaluated for susceptibility to root rot in plots in Puyallup, Washington, in plantings established in Year 8. The presence of *Phytophthora fragariae* var *rubi* ([W. F. Wilcox & J. M. Duncan] W. A. Man in't Veld,) in these root rot plots was verified via PCR. Four plants of each clone were planted in this area. Plants were subjectively rated for vigor in the fall of each year from 0 to 5, with 0 being dead and 5 a healthy and vigorous plant. In the fall of Year 11, 'Cascade Harvest' had a rating of 5.0 for all four plants, while 'Willamette' averaged 1.75 and 'Meeker' averaged 0.5. Based on this trial, 'Cascade Harvest' has a very good level of root rot tolerance.

'Cascade Harvest' tested virus negative after graft inoculation using leaflets from a field grown plant naturally infected with raspberry bushy dwarf virus. Plants of 'Cascade Harvest' that have been exposed to virus infected pollen in the field for over five years have continued to test negative for raspberry bushy dwarf virus. Based on this testing, 'Cascade Harvest' appears to be resistant to raspberry bushy dwarf virus common in Puyallup, Wash.

The intended market use of fruit from the 'Cascade Harvest' plant is as fresh or frozen.

What is claimed:

1. A new and distinct variety of raspberry plant designated as 'Cascade Harvest', as illustrated and described herein.

* * * * *